United States Patent [19]

Lin

[11] 4,256,729
[45] Mar. 17, 1981

[54] N,N'-BIS-(2,3-DIHYDROXYPROPYL)-2,4,6-TRIIODO-5-(2-KETO-L-GULONAMIDO)ISOPHTHALAMIDE AND RADIOLOGICAL COMPOSITIONS CONTAINING SAME

[75] Inventor: Youlin Lin, Chesterfield, Mo.
[73] Assignee: Mallinckrodt, Inc., St. Louis, Mo.
[21] Appl. No.: 23,509
[22] Filed: Mar. 23, 1979
[51] Int. Cl.$^3$ .............................................. A61K 49/04
[52] U.S. Cl. .......................................... 424/5; 536/53; 560/251
[58] Field of Search ............................ 536/53; 424/5; 260/558 A; 560/251

[56] References Cited

U.S. PATENT DOCUMENTS

| | | | |
|---|---|---|---|
| 3,666,760 | 5/1972 | Ackerman | 260/558 A X |
| 3,701,771 | 10/1972 | Almen et al. | 260/558 A X |
| 3,770,820 | 11/1973 | Ackerman | 260/558 A X |
| 4,001,323 | 1/1977 | Felder et al. | 260/559 A |
| 4,125,599 | 11/1978 | Wiegert | 424/5 |

FOREIGN PATENT DOCUMENTS 2726196 12/1977 Fed. Rep. of Germany .
2805928 10/1978 Fed. Rep. of Germany ............ 424/5

OTHER PUBLICATIONS

Chem. Abstracts 85:94103 r.
Chem. Abstracts 87:136300 b (German Offen. 2643841, 4-7-77, pp. 26-28 pertinent).
Chem. Abstracts 83:114021 b.
Chem. Abstracts 88:33890 k.
Chem. Abstracts 88:23337 w.

*Primary Examiner*—Ethel G. Love
*Attorney, Agent, or Firm*—Senniger, Powers, Leavitt and Roedel

[57] ABSTRACT

Novel X-ray contrast agents, i.e., N,N'-bis-(2,3-dihydroxypropyl)-2,4,6-triiodo-5-(2-keto-L-gulonamido)isophthalamide, and intermediates.

6 Claims, No Drawings

N,N'-BIS-(2,3-DIHYDROXYPROPYL)-2,4,6-TRIIODO-5-(2-KETO-L-GULONAMIDO)ISOPHTHALAMIDE AND RADIOLOGICAL COMPOSITIONS CONTAINING SAME

The present invention relates to new compounds, to intermediates for such compounds, to radiological compositions containing such compounds and to the use of such radiological compositions.

Non-ionic contrast agents for intravascular and central nervous system visualization are complex molecules. As is known, the iodine in the molecule provides opacification to the X-rays. The remainder of the molecule provides the framework for transport of the iodine atoms. However, the structural arrangement of the molecule is important in providing stability, solubility and biological safety in various organs. A stable carbon-iodine bond is achieved in most compounds by attaching it to an aromatic nucleus. An enhanced degree of solubility as well as safety is conferred on the molecule by the addition of suitable solubilizing and detoxifying groups.

Several of the features that are desirable for intravascular and central nervous system non-ionic contrast agents are often incompatible so that all such agents represent compromises. In searching for the best compromise, the controlling factors are pharmacological inertness, i.e., in vivo safety, and high water solubility. Thus, the ideal intravascular or central nervous system non-ionic agent represents a compromise in an attempt to obtain the following criteria:

1. Maximum opacification to X-rays
2. Pharmacological inertness
3. High water solubility
4. Stability
5. Selective excretion
6. Low viscosity
7. Minimal osmotic effects An object of the present invention is to provide a non-ionic X-ray contrast agent. Another object of this invention is to provide a non-ionic X-ray contrast agent meeting substantially all the foregoing criteria.

This invention relates to N,N'-bis-(2,3-dihydroxypropyl)-2,4,6-triiodo-5-(2-keto-L-gulonamido)isophthalamide. N,N'-Bis-(2,3-dihydroxypropyl)-2,4,6-triiodo-5-(2-keto-L-gulonamido)isophthalamide is subject to a number of different types of isomerism as is explained below. The present invention extends to all isomers thereof having the 2-keto-gulonamido portion in the L form. As used herein, the term N,N'-bis-(2,3-dihydroxypropyl)-2,4,6-triiodo-5-(2-keto-L-gulonamido)isophthalamide means N,N'-bis-(2,3-dihydroxypropyl)-2,4,6-triiodo-5-(2-keto-L-gulonamido)isophthalamide and all isomers thereof having the 2-keto-gulonamido portion in the L form.

This invention also relates to N,N'-bis-(2,3-diacetoxypropyl)-5-(2,3:4,6-di-O-isopropylidene-2-keto-L-gulonamido)-2,4,6-triiodoisophthalamide, N,N'-bis-(2,3-dihydroxypropyl)-5-(2,3:4,6-di-O-isopropylidene-2-keto-L-gulonamido)-2,4,6-triiodoisophthalamide, and isomers thereof having the 2-keto-gulonamido portion in the L form. Further, it relates to 5-amino-N,N'-bis-(2,3-diacetoxypropyl)-2,4,6-triiodobenzamide, and all isomers thereof. All of these are intermediates useful in preparing the N,N'-bis-(2,3-dihydroxypropyl)-2,4,6-triiodo-5-(2-keto-L-gulonamido)isophthalamide.

N,N'-Bis-(2,3-dihydroxypropyl)-2,4,6-triiodo-5-(2-keto-L-gulonamido)isophthalamide exhibits optical isomerism due to the optical characteristics of the sugar amide.

In general, the L form of the sugar amide has been used in the present work but the D form can equally be used.

Carbon-13 nuclear magnetic resonance spectroscopy (C-13 NMR) has shown that N,N'-bis-(2,3-dihydroxypropyl)-2,4,6-triiodo-5-(2-keto-L-gulonamido)isophthalamide also exhibits geometrical isomerism of the hemi-ketal bond in the cyclic sugar form. The C-13 NMR spectra reveal that the 2-keto-L-gulonyl portion exists in α-pyranose and α-furanose forms in aqueous solution, and that the open chain, the β-pyranose, and the β-furanose forms do not exist in detectable concentrations at room temperature (these forms are illustrated in Table I below). The C-13 NMR spectra also indicate the α-pyranose ring form is the predominant ring form (approximately 90–96%) of the two ring forms and the α-furanose ring form is the minor ring form (10–4%). The chemical shift assignments for the respective carbon atoms are in good agreement with the assignments made by S. J. Angyal and G. S. Bethell, *Australian J. Chem.*, 29, 1249 (1976) for L-sorbose and with those made by T. C. Crawford and G. C. Andrews (Pfizer Laboratories, private communication) for 2-ketogulonic acid (xylo-L-hexulosonic acid) and the methyl ester of 2-keto-L-gulonic acid.

TABLE I

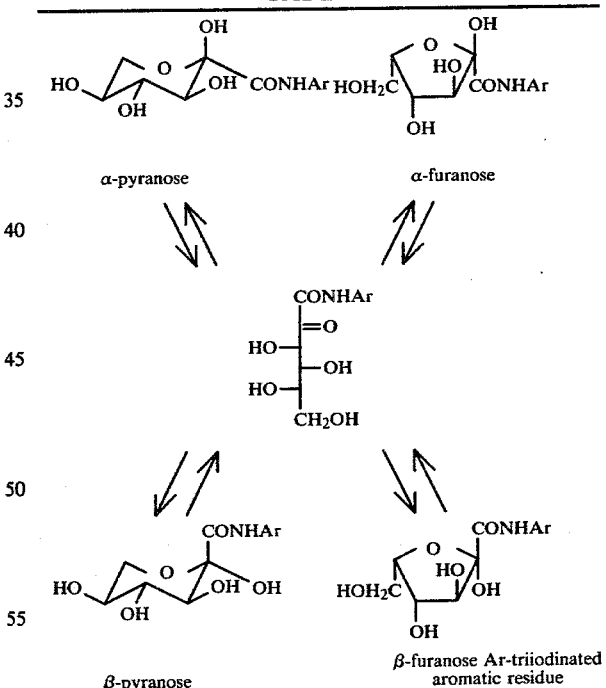

Since N,N'-bis-(2,3-dihydroxypropyl)-2,4,6-triiodo-5-(2-keto-L-gulonamido)isophthalamide has a chiral center in each 2,3-dihydroxypropyl side chain, there are 3 forms which are shown in Table II below. Thus, there are 3 compounds for each sugar residue form (α and β-pyranose, α and β-furanose and open chain). Thus, in theory, there are 15 isomers in solution for N,N'-bis-(2,3-dihydroxypropyl)-2,4,6-triiodo-5-(2-keto-L-gulonamido)isophthalamide.

TABLE II

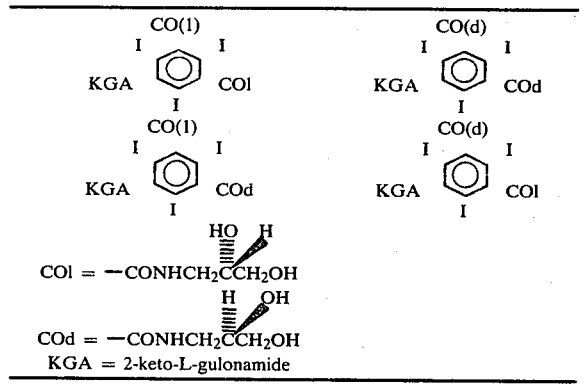

COl = —CONHCH₂C(HO)(H)CH₂OH

COd = —CONHCH₂C(H)(OH)CH₂OH

KGA = 2-keto-L-gulonamide

N,N'-Bis-(2,3-dihydroxypropyl)-2,4,6-triiodo-5-(2-keto-L-gulonamido)isophthalamide may be used as an X-ray contrast agent. The agent may be used in various radiographic procedures including those involving cardiography, coronary arteriography, aortography, cerebral and peripheral angiography, arthrography, intraveneous pyelography and urography as well as myelography. Mixtures of isomers of N,N'-bis-(2,3-dihydroxypropyl)-2,4,6-triiodo-5-(2-keto-L-gulonamido)isophthalamide may also be used as X-ray contrast agents.

A further feature of the present invention is a radiological composition containing N,N'-bis-(2,3-dihydroxypropyl)-2,4,6-triiodo-5-(2-keto-L-gulonamido)isophthalamide as an x-ray contrast agent together with a pharmaceutically acceptable radiological vehicle.

Pharmaceutically acceptable radiological vehicles include those that are suitable for injection such as aqueous buffer solutions, e.g., tris(hydroxymethyl)amino methane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg. Other buffer solutions are described in *Remingtons Practice of Pharmacy, Eleventh Edition*, for example on page 170. The vehicles may contain a chelating amount, e.g., a small amount, of ethylenediaminetetraacetic acid, the calcium disodium salt or other pharmaceutically acceptable chelating agent.

The concentration of N,N'-bis-(2,3-dihydroxypropyl)-2,4,6-triiodo-5-(2-keto-L-gulonamido)isophthalamide in the pharmaceutically acceptable radiological vehicle, for example an aqueous medium, varies with the particular field of use. A sufficient amount is present to provide satisfactory X-ray visualition. For example, when using aqueous solutions for angiography the concentration of iodine is generally 140–400 mg/ml and the dose is 25–300 ml.

The radiological composition is administered so that the contrast agent remains in the living animal body for about 2 to 3 hours, although both shorter and longer residence periods are normally acceptable. N,N'-Bis-(2,3-dihydroxypropyl)-2,4,6-triiodo-5-(2-keto-L-gulonamido)isophthalamide may thus be formulated for vascular visualization conveniently in vials or ampoules containing 10 to 500 ml. of an aqueous solution.

The radiological composition may be used in the usual way in X-ray procedures. For example in the case of selective coronary arteriography, a sufficient amount of the radiological composition to provide adequate visualization is injected into the coronary system, and then the system is scanned with a suitable machine, for example a fluoroscope.

N,N'-Bis-(2,3-dihydroxypropyl)-2,4,6-triiodo-5-(2-keto-L-gulonamido)isophthalamide and the aforementioned intermediates may be prepared in accordance with the procedures set out below. All temperatures are in degrees centigrade.

EXAMPLE I

N,N'-Bis-(2,3-dihydroxypropyl)-2,4,6-triiodo-5-(2-keto-L-gulonamido)isophthalamide (Method I)

I. Preparation

A.

N,N'-Bis-(2,3-dihydroxypropyl)-5-nitroisophthalamide III

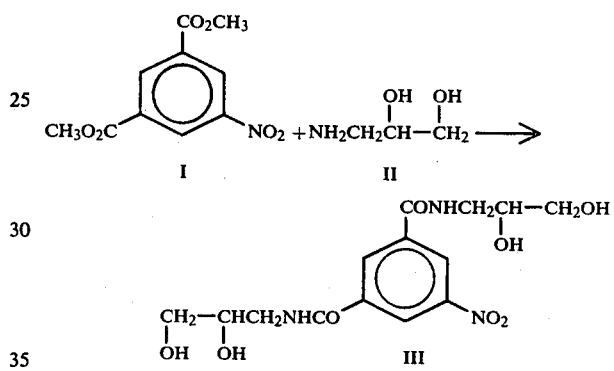

Dimethyl-5-nitroisophthalate (I, 239 g, 1 mole) and 3-amino-1,2-propanediol (II, 85% in glycerol, 300 g, equivalent to 255 g, 2.8 mole) were heated to reflux (67°–69°) in MeOH (800 ml) for 20 hours. MeOH was removed by evaporation (reduced pressure, 50°–60°), the resulting gum was dissolved in water (400 ml) and the solution was evaporated (reduced pressure, 50°–60°) to obtain a gummy residue (492 g). A portion of the residue (369 g) was dissolved in MeOH (400 ml) with warming (50°) and the solution was cooled at −10° overnight to obtain the crystalline product. The slurry was allowed to stand to room temperature and cold MeOH (0°–5°, 300 ml) was added to loosen up the product. The product was collected, washed with cold MeOH (10°, 200 ml×3) and dried (132.5 g, 0.37 mole, 49.5% yield as calculated on purification of ¾ of the crude product). The product showed one spot by tlc analysis (system: 1. Toluene/2-butanone/HCO₂H; 70/25/5; system: 2. EtOAc/MeOH/AcOH, 10/5/1). The product was used in the following hydrogenation and iodination reaction. A portion of the product was recrystallized by dissolving the material (44 g) in boiling MeOH (500 ml) and cooling the solution to −10°. The product was collected and dried (60°, vacuum) (30 g), m.p. 129°–133°, reported m.p. 128°–132° (German Offenlegungsschrift No. 2,726,196, Nyegaard & Co. A/S).

B.
5-Amino-N,N'-bis-(2,3-dihydroxypropyl)-2,4,6-triiodoisophthalamide IV

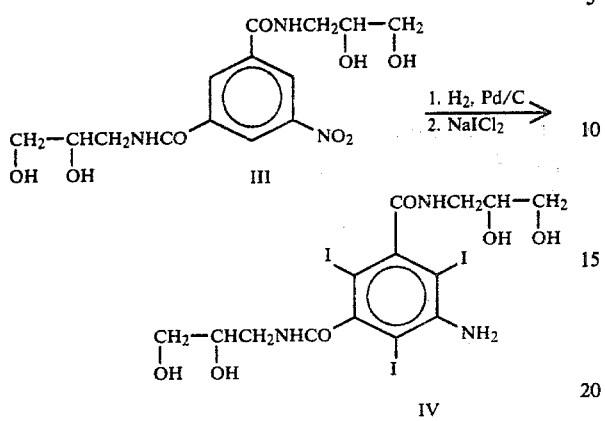

Compound III (89.25 g, 0.25 mole) was suspended in water (1.25 liters) in a 2-liter hydrogenation flask, conc. HCl (21 ml) and 5% Pd/C (2.7 g) were added, and the solution was swirled. The solution was subjected to hydrogenation in a Parr shaker for 2.5 hours. The solution was then filtered, the filtrate was placed in a 3-liter, 3-necked flask equipped with a mechanical stirrer, a condenser, a dropping funnel and a thermometer. The solution was stirred and heated to 80°, and NaICl$_2$ solution (2.35 N, 351 ml, 0.825 mole) was added slowly over a period of one hour at 80~90°. The solution was then heated at 80~90° for 2.5 hours and stirred at room temperature overnight.

The solution (1.85 liters) was evaporated at 50~60° to 450 ml, and the solid (NaCl) which precipitated during the evaporation was removed by filtration. The filtrate was washed with EtOAc (400 ml) and evaporated at 250 ml to precipitate more NaCl. The NaCl was removed, and the filtrate was evaporated to dryness to obtain a glassy residue (177 g). The residue (168 g) was dissolved in boiling MeOH (500 ml), and the solution was dripped into stirring isopropyl alcohol (iPrOH) (1 liter). Some gummy material precipitated from the solution. The supernatant was decanted, cooled to room temperature and evaporated at 800 ml at 50° under reduced pressure. During the evaporation the product precipitated. The solution was cooled to room temperature, and the product was collected and dried (55.3 g, the product as p$_1$).

The above gummy material was dissolved in boiling MeOH (300 ml), and the solution was dripped into stirring hot iPrOH (70°, 900 ml). The warm supernatant was decanted from a small amount of a gummy precipitate and evaporated (at 40~50°, reduced pressure) to 800 ml. During the evaporation, more product precipitated. The slurry was cooled to room temperature, and the compound was collected and dried (36.0 g, the product as p$_2$).

The two products, p$_1$ and p$_2$, showed essentially one spot by tlc analysis and had identical R$_f$ values (tlc system 1. CHCl$_3$/MeOH 70/30, system 2. EtOAc/MeOH/AcOH 10/5/1). The products were combined to give 91.3 g (0.13 mole, 54.6% yield as based on purification of 168 g of the crude product) of material. Nmr data are consistent with the assigned structure IV. 3.0 g of the product was recrystallized from boiling iPrOH. The recrystallized compound sintered at 178~183°, melted at 183~186° and decomposed at 210~220°. The compound was reported to sinter at 177~179° and decompose at 195° (German Offenlegungsschrift, No. 2,726,196, Nyegaard & Co. A/S).

C.
5-Amino-N,N'-bis-(2,3-diacetoxypropyl)-2,4,6-triiodoisophthalamide V

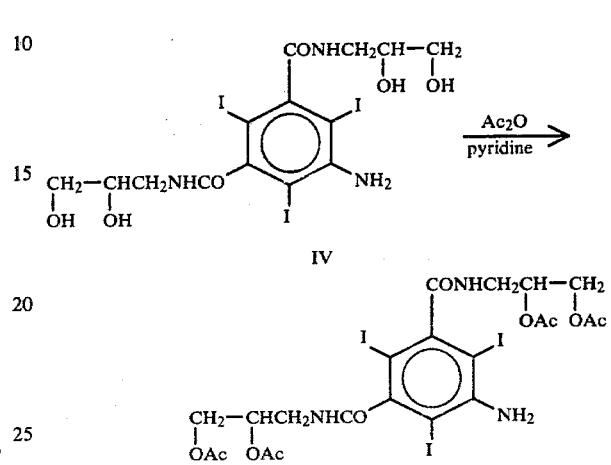

Compound IV (88.13 g, 0.125 mole) was dissolved in pyridine (300 ml) and to the stirring solution, Ac$_2$O (63.82 g, 0.625 mole) was added slowly. An ice bath was occasionally used to maintain the reaction mixture below 45°. After the addition of Ac$_2$O, the reaction mixture was allowed to stir at room temperature overnight (16 hours).

Next, the reaction mixture was dripped slowly into stirring water (4 liters), and the solution was stirred at room temperature for 1 hour (pH 5.8). The solution was adjusted to pH 2 with conc. HCl (320 ml) and extracted with CHCl$_3$ (1 liter and 500 ml×2). The CHCl$_3$ extracts were combined, washed with water (800 ml×2), dried over anhydrous Na$_2$SO$_4$ and evaporated (50°-60°, reduced pressure) to obtain a white glassy product. The product was dried at 60° under vacuum (5 hours) to give 102.0 g (0.1168 mole, 93.5% yield) of material. Tlc analysis showed essentially one spot in two systems: 1. EtOAc/CH$_2$Cl$_2$, 30/20; 2. EtOAc/CHCl$_3$/AcOH, 30/20/1. Nmr data are consistent with the structure V.

N,N'-Bis-(2,3-diacetoxypropyl)-5-(2,3:4,6-di-O-isopropylidene-2-keto-L-gulonamido)-2,4,6-triiodoisophthalamide VIII

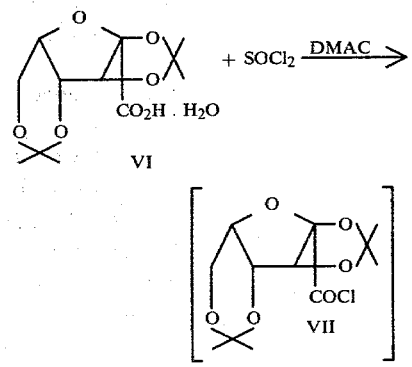

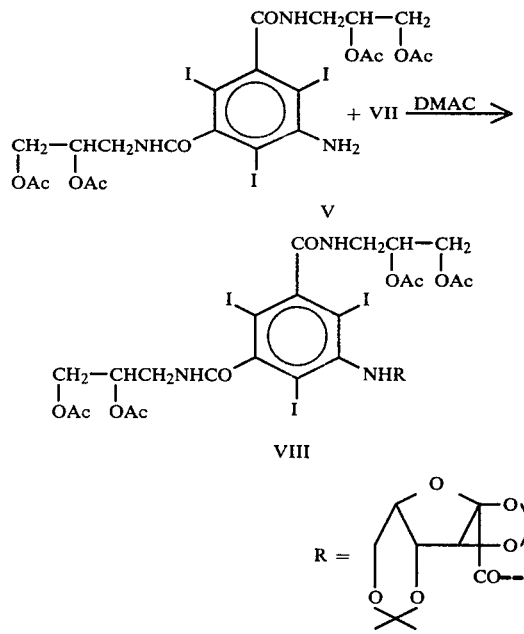

In a 2-liter flask equipped with a CaCl₂ drying tube, a mechanical stirrer and a thermometer reaching into the reaction solution, compound VI (146.14 g, 0.5 mole, Hoffman-LaRoche) in N,N-dimethylacetamide (DMAC) (500 ml) was cooled to −10° (methanol-ice bath). To the stirring solution was added thionyl chloride (0.9 mole, 107.1 g; 65.4 ml) dropwise so that the reaction temperature was maintained at −5° to −10°. After the addition (about 1 hour), the reaction mixture was stirred at −10° to −5° for 1 hour, 0° for the second and 0°–10° for the third hour.

The solution was then cooled to 0°, compound V (87.3 g, 0.1 mole) was added as powder, and 70 ml of DMAC was used to rinse the powder off the walls of the flask. The ice-water bath was removed, and the reaction mixture was stirred at room temperature continuously for 4 days.

The reaction mixture was poured slowly into stirring 5% NaHCO₃ (6.5 liters) so that no overflow of the foamy solution occurred. Some gummy material precipitated during the addition. The solution was allowed to stir for 30 minutes and was extracted with CHCl₃ (1.2 liters and 0.6 liters×2). The combined CHCl₃ layers were washed with 5% NaHCO₃ (3 liters and 1.5 liters) and saturated NaCl (1.2 liters×2), dried over anhydrous Na₂SO₄ (550 g) and was evaporated (55°, reduced pressure) to give a glassy solid (124.5 g, >100% crude yield due to the presence of DMAC). The crude product was used in the following hydrolysis reaction without removal of residual DMAC. The product showed essentially one spot by tlc analysis (system: 1. EtOAc/CHCl₃/AcOH, 30/20/1; 2. EtOAc/CH₂Cl₂, 30/20). Nmr data are consistent with the assigned structure VIII.

N,N'-Bis-(2,3-dihydroxypropyl)-2,4,6-triiodo-5-(2-keto-L-gulonamido)isophthalamide IX

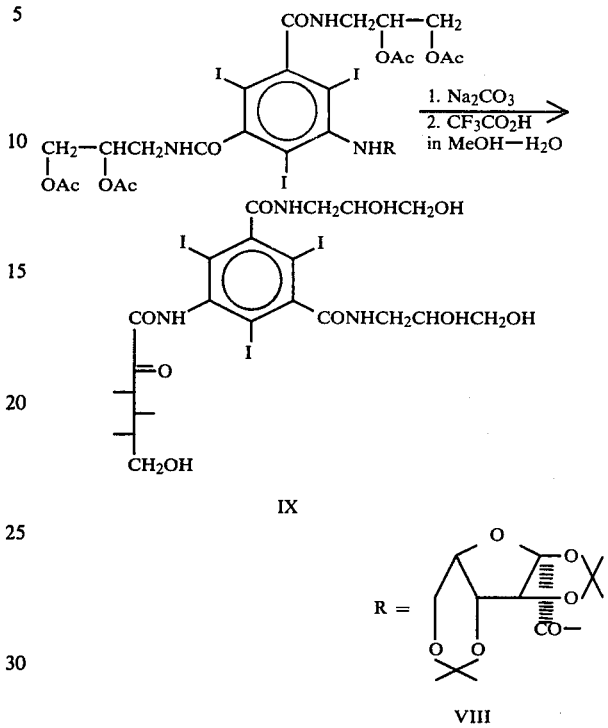

Compound VIII (crude product from Step D, 124.5 g, theoretical weight 112.9 g, 0.1 mole) in MeOH (600 ml) was diluted with water (600 ml) containing anhydrous Na₂CO₃ (26.5 g, 0.25 mole), and the solution was stirred for 2 hours at room temperature to hydrolyze the acetate groups and provide N,N'-bis-(2,3-dihydroxypropyl)-5-(2,3:4,6-di-O-isopropylidene-2-keto-L-gulonamido)-2,4,6-triiodoisophthalamide. The solution (pH 10.7) was then acidified with CF₃CO₂H (75 ml) to pH 1.0 and refluxed at 78° for 17 hours.

The solution was evaporated to 600 ml, washed with CHCl₃-iPrOH (3:1, 600 ml and 400 ml×2) and evaporated to 400 ml. The solution was passed through an ion-exchange column (size: 5×20 cm) containing 1.5 liters of IR-120 (resin marketed by Mallinckrodt under the trade designation Amberlite, 1.75 meq. H⊕/ml). MeOH—H₂O (1:1) was used as the solvent and 12 fractions (200–300 ml) were collected. The fractions (3–10) containing the product were combined and evaporated (60°–65°, reduced pressure) to give a glassy solid (94.8 g). The product showed a major spot with a higher $R_f$ minor impurity by tlc analysis (system: CHCl₃/MeOH/AcOH, 70/30/2). The solid was dissolved in boiling MeOH (550 ml) and the solution was dripped into stirring hot (about 60°) iPrOH (1.1 liters). The compound precipitated immediately as a white powder. The slurry was stirred continuously while cooling to room temperature, and the product was collected. The product was redissolved in boiling MeOH (800 ml) and dripped into stirring hot (60°) iPrOH (1.1 liters). The resulting slurry was stirred continuously while cooling to room temperature, and the product collected (86 g). The product was again dissolved in boiling MeOH (700 ml). The solution was dripped into stirring hot (60°) iPrOH (1.4 liters). The resulting slurry was stirred while cooling to room temperature, and the product was collected.

The product was dissolved in water (sterile water for injection, 1 liter). The solution was evaporated to about 800 ml under reduced pressure at 55° and treated with active charcoal (Darco G-60, 7.0 g) at room temperature overnight. The solution was filtered (first through a Whatman #4 filter paper and then through a Millipore 0.22 μ filter paper), and the clear filtrate was evaporated under reduced pressure at 50°–60° to give a white glassy solid. The product, which was dried under vacuum at 50°–60° for 5 hours, weighed 53.0 g (60% yield). The compound softens at 190°–195° and decomposes above 220°. Tlc analysis showed one spot for the product in 3 systems (1.n-BuOH/H₂O/AcOH; 100/30/50, 2.i-BuOH/iPrOH/conc. NH₄OH, 10/4/4; 3. CHCl₃/CH₃OH/AcOH; 70/30/2). Nmr and ir data are consistent with the assigned structure IX. Elemental analysis: Calcd. for $C_{20}H_{26}I_3N_3O_{12}$: C, 27.26; H, 2.97; I, 43.21; N, 4.77; Found: C, 26.92; H, 3.15; I, 42.92; N, 4.40. The compound is highly soluble in water ($\geq$100%) and is stable in aqueous solution by tlc and lc analysis.

EXAMPLE II

N,N'-Bis-(2,3-dihydroxypropyl)-2,4,6-triiodo-5-(2-keto-L-gulonamido)isophthalamide (Method II)

A. Synthesis of 3-Amino-1,2-propanediol $$ClCH_2CHOHCH_2OH + H_3N + NaOH \rightarrow H_2NCH_2CHOHCH_2OH + H_2O + NaCl$$

In a 22-liter reaction flask equipped with an ice bath, mechanical stirrer, dry ice condenser, thermometer, and gas inlet tube was placed methanol (14 liters). Sodium hydroxide (600 g, 15.0 mole) was added, and when the solution temperature fell below 15° C., gaseous anhydrous ammonia (4350 ml, 3900 g, 230 mole) was added until the solution level reached the predetermined mark. 3-Chloro-1,2-propanediol (1650 g, 15.0 mole) was then added, the ice bath and condenser were removed, and stirring was continued for 20 hours (final temperature 20° C.). The solution volume was reduced to 3 liters by atmospheric pressure distillation on a rotary evaporator, and the NaCl which had precipitated was filtered and rinsed with methanol (3 liters). The combined organic solutions were again concentrated to a volume of 3 liters, and isopropanol (1.5 liters) was added. The sodium chloride precipitate was filtered, rinsed with isopropanol (250 ml), and the combined organic solutions were fractionally distilled. Distillation of the residue (129°–145° C. at 4 mm) afforded 3-amino-1,2-propanediol (772 g, 57%) as a light orange oil. This material was one spot ($R_f$=0.23) by tlc (utilizing a plate marketed by Mallinckrodt under the trade designation ChromAR Plate, 70:30:2 chloroform:methanol: acetic acid, sulfuric acid/charring visualization).

B. Synthesis of
N,N'-Bis-(2,3-dihydroxypropyl)-5-nitroisophthalamide

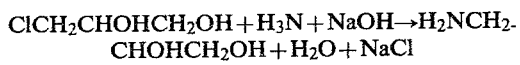

$$+ H_2CH_2CHOHCH_2OH \longrightarrow$$

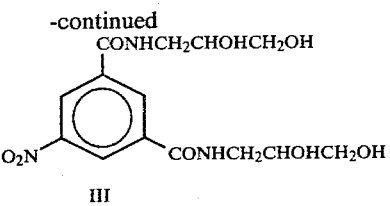

The amine II (893 g, 9.8 mole) prepared according to the procedure set forth in step A above and diester I (838 g. 3.5 mole) were mixed in methanol (2.8 liters) and heated at reflux for 7 hours. During the last 0.5 hour, the methanol was allowed to distill (~400 ml). After the solution had cooled at −10° for 16 hours, the solids were filtered, rinsed with methanol (1 liter) and dried to give the desired amide III (189 g, 15%).

Ether (400 ml) was added to the mother liquor. After this solution had cooled at −10° for 6 hours, the solids were filtered, rinsed with methanol, and air-dried to give additional III (286 g, 23%).

The mother liquors were cooled to −10° for 4 days and filtered. The solids were filtered, rinsed with methanol (500 ml) and dried at 70° overnight to give an additional crop of III (486 g, 39%). The overall yield was 961 g (77%). Tlc (utilizing a plate marketed by Mallinckrodt under the trade designation ChromAR plate, 10:5:1 ethyl acetate:methanol:acetic acid, $R_f$=0.65) showed primarily a single spot with a small amount (<2%) of baseline material.

C. Synthesis of
5-Amino-N,N'-bis-(2,3-dihydroxypropyl)-2,4,6-triiodoisophthalamide

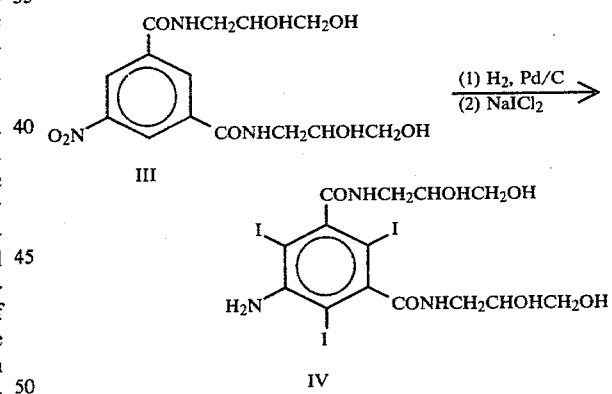

Nitrodiamide III (211.0 g, 0.59 mole) prepared according to the procedure set forth in step B above was suspended in water (1.2 liters) in a 2-liter Parr shaker bottle, and concentrated HCl (50 ml) was added followed by 5% Pd/C as catalyst (6.4 g). The atmosphere was replaced with hydrogen, and the reaction was shaken under hydrogen atmosphere at 15–45 psi until gas uptake ceased (about 3.5 hours). The catalyst was filtered and rinsed with water (50 ml).

The resulting colorless aqueous solution was transferred to a 3-liter, 3-necked, round-bottomed flask equipped with a mechanical stirrer, addition funnel, thermometer, and oil bath, and heated to 80° C. Sodium iododichloride (805 ml of a 2.42 molar solution, 1.95 moles) was added over a 45-minute period while the temperature was maintained at 80°–82° C. Stirring was then continued at 83°–85° C. for 2.5 hours, the reaction was allowed to stand at room temperature for 16 hours, seeded, and allowed to stand at −5° for 24 hours. The solids were filtered off, rinsed with water (1 liter), and air-dried to give the desired compound IV (280.4 g, 67%) as a light pink solid. Tlc (utilizing a plate marketed by Mallinckrodt under the trade designation ChromAR plate, 70:30:2 chloroform:methanol:acetic acid, $R_f=0.70$) indicated only a single compound to be present.

D. Synthesis of 5-Amino-N,N'-bis-(2,3-diacetoxypropyl)-2,4,6-triiodoisophthalamide

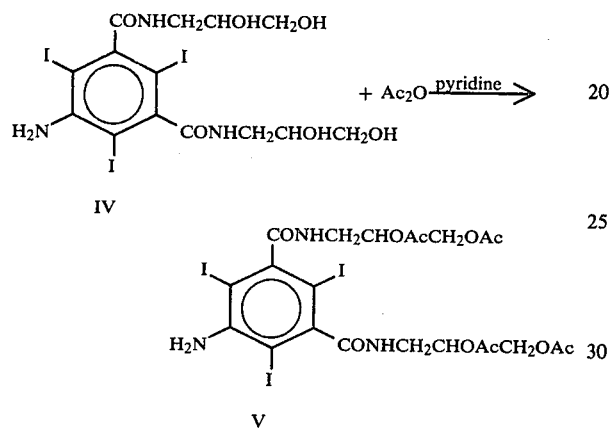

In a 3-liter, 3-necked, round-bottomed flask equipped with a thermometer, mechanical stirrer and addition funnel were mixed the tetraol IV (530 g, 0.752 mole) prepared in the same manner as set forth in step C above, and pyridine (1800 ml). Acetic anhydride (384 g, 3.76 mole, 5.0 equivalents) was then added over a 20-minute period, and an ice-water bath was used to keep the temperature below 45° C. An oil bath was then added, and the reaction was stirred at 40°–45° C. for one hour, then at room temperature for 17 hours.

The reaction mixture was poured with rapid stirring into ice-water (12 liters) and stirred for 30 minutes. The aqueous solution was decanted from the gum which formed and was extracted three times with chloroform (1 liter). The combined organic extracts were added to the gum and stirred for 30 minutes with cold saturated sodium bicarbonate solution (12 liters). The layers were separated, and the aqueous solution was extracted with chloroform (500 ml). The combined organic solutions were rinsed four times with cold dilute (10%) hydrochloric acid (2 liters). The organic solution was dried over sodium sulfate, filtered, and rotary evaporated to give the tetraacetate V (659 g, 100%) as a light purple foam. Tlc (utilizing a plate marketed by Mallinckrodt under the trade designation ChromAR plate, 30:20:1 ethyl acetate-chloroform:acetic acid, $R_f=0.34$) showed the product to be 98% pure (est.) with two impurities having $R_f$s of 0.10 (1%) and 0.05 (1%). This material could be used without further purification.

E. Synthesis of N,N'-bis-(2,3-diacetoxypropyl)-5-(2,3:4,6-di-O-isopropylidene-2-keto-L-gulonamido)-2,4,6-triiodoisophthalamide

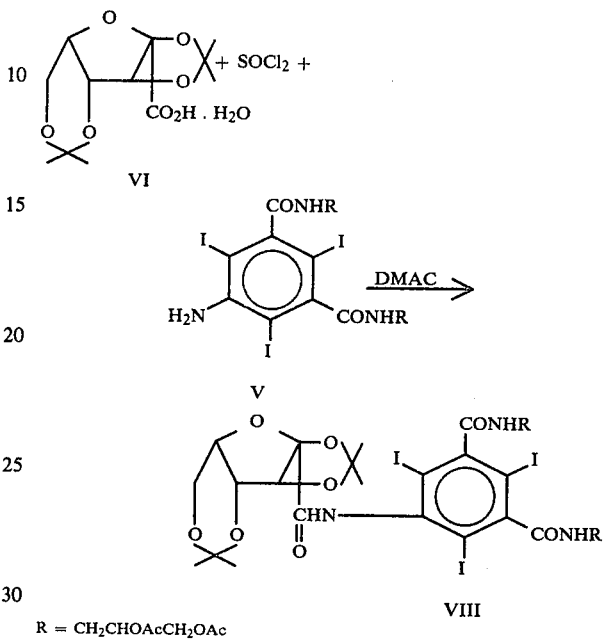

In a 12-liter, 3-necked, round-bottomed flask equipped with a thermometer, mechanical stirrer, addition funnel, and drying tube were mixed diacetone-2-keto-L-gulonic acid monohydrate VI (1200.0 g, 4.11 mole) and DMAC (2750 ml). This solution was cooled to −10° C., and the thionyl chloride (876.6 g, 7.37 mole) was added over a 70-minute period so as to maintain a reaction temperature of −10° C. to −5° C. After the addition was complete, stirring was continued at −10° to −5° C. for one hour, at −5° to 0° C. for one hour, and at 0° to 10° for one hour. The solution was cooled to 0°, and the amine V (715.5 g, 0.819 mole, 1.0 eq) was added as a powder followed by additional DMAC (380 ml). After it had stirred at room temperature for 17 hours, the dark reaction was poured carefully into cold saturated sodium bicarbonate solution (40 liters), and after this mixture had stirred for 15 minutes, ethyl acetate (8 liters) was added. The resulting mixture was stirred for an additional 30 minutes, and the layers were separated. The aqueous portion was extracted two additional times with ethyl acetate (4 liters), and the combined organic extracts were rinsed twice with saturated sodium bicarbonate solution (2 liters), once with water (1 liter), and dried over sodium sulfate. Filtration and rotary evaporation afforded VIII (881.7 g 96%) as a solid brown foam. Tlc (utilizing a plate marketed by Merck, two developments, once with chloroform, then once with ethyl acetate) indicated primarily one compound ($R_f=0.69$) with minor impurities with $R_f$s at 0.86, 0.76, 0.27, 0.18, and 0.00. This material which was at least 90% pure by tlc analysis was used without further purification.

F. Synthesis of N,N'-bis-(2,3-dihydroxypropyl)-2,4,6-triiodo-5-(2-keto-L-gulonamido)isophthalamide

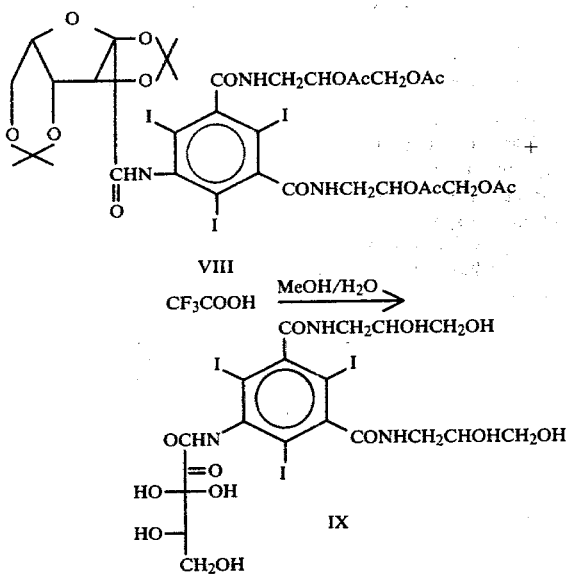

Compound VIII (1092.5 g, 0.967 mole, 1 eq) prepared according to the procedure set forth in step E above was dissolved in methanol (4.8 liters) in a 12-liter, 3-necked, round-bottomed flask equipped with a mechanical stirrer, thermometer, reflux condenser, and heating mantle. Water (4.8 liters) was then added followed by trifluoroacetic acid (550 g, 4.82 mole). The reaction was heated to reflux (pot temperature 66°–70° C.) for 24 hours. Tlc (utilizing a plate marketed by Mallinckrodt under the trade designation ChromAR plate, 70:30:2 chloroform:methanol:acetic acid) then indicated the reaction was complete, so the solvent was removed by rotary evaporation to give a foam residue (908 g).

This material was dissolved in methanol (5.3 liters) at 60°, and the resulting solution was added slowly (5.5 hours) to 2-propanol (10.6 liters) at 60°. Rapid stirring at 60° for 15 minutes was followed by addition of an ice-water bath and stirring for an additional 45 minutes (reaction temperature 25° C.). The solids were filtered, rinsed with 2-propanol (1.5 liters), pressed dry with a rubber dam, and dried in open trays overnight to give a moist tan powder (983 g, 115%). The once-crystallized product was dissolved in methanol (7.5 liters) at 60°, and the resulting solution was slowly added (4 hours) to 2-propanol (10.6 liters) at 60° C. After stirring at 60° C. for 30 minutes, the mixture was cooled in an ice bath to 22° (45 minutes) and the solids were then filtered, rinsed with 2-propanol (1.5 liters), pressed dry, and air dried overnight to give a light (still wet) tan powder (908 g).

The twice-precipitated material was dissolved in water (4 liters) and stirred with charcoal (marketed under the trade designation DARCO G-60, 48 g) for 30 minutes. After the charcoal was filtered and rinsed with water (200 ml), the pH was 5.10. A mixed bed resin (from Barnstead Company D5041 mixed resin cartridge, 742 g) was then added, and after this solution had stirred at room temperature for one hour, the resin was filtered and rinsed three times with water (1 liter). The combined aqueous solutions were stirred four additional times for 30 minutes with the charcoal (48 g). After each treatment the solution was filtered, and the carbon was rinsed with water (100 ml). After the final carbon treatment, the solution was filtered utilizing a filter (0.22 $\mu$) marketed under the trade designation Millipore, combined with the material prepared in a previous run, and dried in vacuo. The combined yield was 644 g (46% yield) of IX as an off-white (peach) foam.

Analytical Results

1. Appearance: off-white glassy powder
2. Solubility: $\geq$100% w/v.
3. pH: 5.58 of a 5% (w/v) solution.
4. LOD: 3.14% by Karl Fischer titration.
5. Tlc: 1 spot ($R_f$=0.56) in 10:3:5 n-butanol:water:acetic acid. 1 spot ($R_f$=0.16) in 70:30:2 chloroform:methanol:acetic acid.
6. Lc: 1 peak (retention time=11.5 minutes) in water (plus acetic acid to pH 4.13), flow rate =1.0 ml/min.
7. NMR: consistent with assigned structure.
8. IR: consistent with assigned structure.
9. Elemental Analysis: Calculated for $C_{20}H_{26}I_3N_3O_{12}$: C, 27.26; H, 2.97; I, 43.21; N, 4.77. Found: C, 27.22; H, 3.33; I, 42.32; N, 4.92.

EXAMPLE III

Radiographic Observations

A male mouse (20 g) was anesthetized with sodium pentobarbital (60 mg/kg, i.p.; Diabutal®, Diamond Laboratories). The N,N'-bis-(2,3-dihydroxypropyl)-2,4,6-triiodo-5-(2-keto-L-gulonamido)isophthalamide prepared by Method I, 10,000 mg I/kg (28% I solution), I.V. was injected via a lateral tail vein at a rate of ½ ml/minute. Whole body radiographs in the lateral and ventraldorsal positions were taken immediately after administration with opacification of the cardiovascular and renal excretory systems.

A pentobarbital anesthetized male rat received 140 mg I/kg of the N,N'-bis-(2,3-dihydroxypropyl)-2,4,6-triiodo-5-(2-keto-L-gulonamido)isophthalamide prepared by Method I, (28% I solution) intracisternally. Lateral radiographs of the head and thorax were obtained immediately and 3 minutes after contrast administration with good visualization of the cisterna magna, basal cisterns, and cervical subarachnoid space.

EXAMPLE IV

The following pharmacological studies were conducted on N,N'-bis-(2,3-dihydroxypropyl)-2,4,6-triiodo-5-(2-keto-L-gulonamido)isophthalamide prepared by Method II (PRODUCT).

1. Acute Intraveneous Toxicity in Mice

A solution of the PRODUCT was injected into the lateral tail vein of young adult male and female Swiss mice at a rate of 1 ml/min. Following injections, the animals were observed for immediate reactions and then daily throughout a seven day observation period. The $LD_{50}$ values were calculated by the method of Litchfield and Wilcoxon (*J. Pharmacol. Exp. Therap.* 96: 99–113, 1949) with the following results.

| Concentration | $LD_{50}$/(95% Confidence Limits) | |
|---|---|---|
| (mg I/ml) | mg I/kg | mg/kg |
| 400 | 19,300 | 44,666 |

| Concentration | LD₅₀/(95% Confidence Limits) | |
|---|---|---|
| (mg I/ml) | mg I/kg | mg/kg |
| | (18,161–20,510) | (42,030–47,466) |

2. Acute Intracerebral Toxicity in Mice

Employing a slightly modified version of the techique developed by Haley and McCormick (*Brit. J. Pharmacol.* 12: 12–15, 1957), young adult male and female Swiss mice received injections of a solution of the PRODUCT directly into lateral ventricles and brain tissue. Following injections the animals were observed for immediate reactions and then daily throughout a seven day observation period. The LD$_{50}$ values were calculated by the method of Litchfield and Wilcoxon (*J. Pharmacol. Exp. Therap.* 96: 99–113, 1949) with the following results.

| Concentration Range | LD₅₀/(95% Confidence Limits) | |
|---|---|---|
| (mg I/ml) | mg I/kg | mg/kg |
| 250–400 | 1,460 | 3,379 |
| | (1,203–1,772) | (2,784–4,101) |

3. Acute Intracisternal Toxicity in Rats

The technique described by Melartin et al. (*Invest. Radiol.* 5: 13–21, 1970) was utilized to evaluate lethal effects of a solution of the PRODUCT after injection into cerebrospinal fluid at the cisterna magna. Young adult male and female Sprague Dawley rats were used. After dosing, the animals were housed individually and observed for immediate reactions and periodically for a two day observation period. The LD$_{50}$ values were calculated by the method of Litchfield and Wilcoxon (*J. Pharmacol. Exp. Therap.* 96: 99–113, 1949) with the following results.

| Concentration | LD₅₀/(95% Confidence Limits) | |
|---|---|---|
| (mg I/ml) | mg I/kg | mg/kg |
| 444 | 744 | 1,722 |
| | (582–951) | (1,347–2,201) |

4. Acute intracisternal Neurotoxicity in Dogs

Adult dogs of either sex were employed for this procedure and were briefly anesthetized with thiopentol sodium during the injection of a solution of the compound. The PRODUCT was administered into cerebrospinal fluid at the cisterna magna at varying concentrations but at a constant 0.5 ml/kg volume dose. Animals were thereafter observed for neurotoxicity with the following results.

| Dosage Range (mg I/kg) | Minimum Convulsion Dose (mg I/kg) |
|---|---|
| 200–244 | >244* |

What is claimed:

1. N,N'-Bis-(2,3-dihydroxypropyl)-2,4,6-triiodo-5-(2-keto-L-gulonamido)isophthalamide.

2. A radiological composition containing N,N'-bis-(2,3-dihydroxypropyl)-2,4,6-triiodo-5-(2-keto-L-gulonamido)isophthalamide in a sufficient amount to provide satisfactory X-ray visualization together with a pharmaceutically acceptable radiological vehicle.

3. In a method for X-ray visualization wherein a radiological composition containing an X-ray contrast agent in a pharmaceutically acceptable radiological vehicle is injected in a sufficient amount to provide adequate visualization and thereafter x-ray visualization carried out, the improvement comprising utilizing as the radiological composition a composition containing N,N'-bis-(2,3-dihydroxypropyl)-2,4,6-triiodo-5-(2-keto-L-gulonamido)isophthalamide in a sufficient amount to provide satisfactory X-ray visualization together with a pharmaceutically acceptable radiological vehicle.

4. N,N'-Bis-(2,3-diacetoxypropyl)-5-(2,3:4,6-di-O-isopropylidene-2-keto-L-gulonamido)-2,4,6-triiodoisophthalamide.

5. N,N'-Bis-(2,3,-dihydroxypropyl)-5-(2,3:4,6-di-O-isopropylidene-2-keto-L-gulonamido)-2,4,6-triiodoisophthalamide.

6. 5-Amino-N,N'-bis-(2,3-diacetoxypropyl)-2,4,6-triiodoisophthalamide.

* * * * *

UNITED STATES PATENT AND TRADEMARK OFFICE
CERTIFICATE OF CORRECTION

PATENT NO. : 4,256,729
DATED : March 17, 1981
INVENTOR(S) : Youlin Lin

It is certified that error appears in the above—identified patent and that said Letters Patent is hereby corrected as shown below:

Column 9, line 22, "($\geqq$)" should read --($\geq$--; line 65, "+H$_2$CH" should read --+H$_2$NCH--. Column 14, line 12, "$\geqq$" should read --$\geq$--. Column 16, line 20, "Convulsion" should read --Convulsive--; after "244*" the following footnote should be inserted --*Highest dose given at or below which no evidence of convulsive activity was observed; but at which death from respiratory arrest occurred.--

Signed and Sealed this

Second Day of June 1981

[SEAL]

Attest:

RENE D. TEGTMEYER

Attesting Officer

Acting Commissioner of Patents and Trademarks